(12) United States Patent
Crotty et al.

(10) Patent No.: US 10,426,424 B2
(45) Date of Patent: Oct. 1, 2019

(54) SYSTEM AND METHOD FOR GENERATING AND PERFORMING IMAGING PROTOCOL SIMULATIONS

(71) Applicant: General Electric Company, Schenectady, NY (US)

(72) Inventors: Dominic Joseph Crotty, Waukesha, WI (US); Franco Rupcich, Wauwatosa, WI (US); John Howard Londt, Oconomowoc, WI (US); Mark Vincent Profio, Elm Grove, WI (US); Darin Robert Okerlund, Muskego, WI (US); Roy-Arnulf Helge Nilsen, Waukesha, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 154 days.

(21) Appl. No.: 15/819,394

(22) Filed: Nov. 21, 2017

(65) Prior Publication Data
US 2019/0150872 A1    May 23, 2019

(51) Int. Cl.
*A61B 6/00* (2006.01)
*G16H 30/40* (2018.01)
*A61B 6/03* (2006.01)
*G16H 40/63* (2018.01)

(52) U.S. Cl.
CPC .......... *A61B 6/545* (2013.01); *A61B 6/032* (2013.01); *A61B 6/465* (2013.01); *G16H 30/40* (2018.01); *G16H 40/63* (2018.01)

(58) Field of Classification Search
None
See application file for complete search history.

(56) References Cited

U.S. PATENT DOCUMENTS

| | | | |
|---|---|---|---|
| 3,581,624 | A | 6/1971 | Stone et al. |
| 4,009,344 | A | 2/1977 | Flemming |
| 4,430,699 | A | 2/1984 | Segarra et al. |
| 4,736,363 | A | 4/1988 | Aubin et al. |

(Continued)

FOREIGN PATENT DOCUMENTS

| | | |
|---|---|---|
| CN | 101170549 A | 4/2008 |
| CN | 101596112 A | 12/2009 |

(Continued)

*Primary Examiner* — Hoon K Song
(74) *Attorney, Agent, or Firm* — Fletcher Yoder, P.C.

(57) ABSTRACT

A computer-implemented method for generating and simulating a computed tomography (CT) protocol is provided. The method includes receiving, via a graphical user interface, at a processor user input including patient population size settings and scan technique settings for modeling the effects of the scan technique settings across a patient population as a function of patient size. The method also includes generating, via the processor, a patient population profile based on at least the patient population size settings and the scan technique settings, wherein the patient population profile includes specific CT scan technique settings to be applied across different size ranges of the patient population as a function of patient size. The method further includes displaying, on the graphical user interface, one or more visualization elements illustrating the effect of these specific CT scan technique settings on specific imaging metrics across the patient population.

20 Claims, 4 Drawing Sheets

(56) References Cited

U.S. PATENT DOCUMENTS

| | | |
|---|---|---|
| 4,794,534 A | 12/1988 | Millheim |
| 4,891,829 A | 1/1990 | Deckman et al. |
| 5,079,766 A | 1/1992 | Richard et al. |
| 5,208,846 A | 5/1993 | Hammond et al. |
| 5,218,680 A | 6/1993 | Farrell et al. |
| 5,250,019 A | 10/1993 | McGinley |
| 5,268,300 A | 12/1993 | Latura et al. |
| 5,341,292 A | 8/1994 | Zamenhof |
| 5,550,760 A | 8/1996 | Razdan |
| 5,583,902 A | 12/1996 | Bae |
| 5,612,895 A | 3/1997 | Balaji et al. |
| 5,687,208 A | 11/1997 | Bae et al. |
| 5,694,579 A | 12/1997 | Razdan et al. |
| 5,713,075 A | 1/1998 | Threadgill et al. |
| 5,717,830 A | 2/1998 | Sigler et al. |
| 5,722,411 A | 3/1998 | Suzuki et al. |
| 5,761,429 A | 6/1998 | Thompson |
| 5,786,770 A | 7/1998 | Thompson |
| 5,810,007 A | 9/1998 | Holupka et al. |
| 5,838,687 A | 11/1998 | Ramfelt |
| 5,838,913 A | 11/1998 | Lysejko et al. |
| 5,842,125 A | 11/1998 | Modzelesky et al. |
| 5,842,987 A | 12/1998 | Sahadevan |
| 5,913,164 A | 6/1999 | Pawa et al. |
| 5,937,202 A | 8/1999 | Crosetto |
| 5,956,372 A | 9/1999 | Vaman et al. |
| 5,981,699 A | 11/1999 | Draetta et al. |
| 6,011,830 A | 1/2000 | Sasin et al. |
| 6,055,430 A | 4/2000 | Cooper et al. |
| 6,055,985 A | 5/2000 | Bae et al. |
| 6,061,365 A | 5/2000 | Yeung et al. |
| 6,063,108 A | 5/2000 | Salansky et al. |
| 6,083,163 A | 7/2000 | Wegner et al. |
| 6,112,083 A | 8/2000 | Sweet et al. |
| 6,123,733 A | 9/2000 | Dalton |
| 6,131,809 A | 10/2000 | Drescher et al. |
| 6,150,179 A | 11/2000 | Went |
| 6,175,560 B1 | 1/2001 | Bhagalia et al. |
| 6,185,197 B1 | 2/2001 | Yeung et al. |
| 6,185,409 B1 | 2/2001 | Threadgill et al. |
| 6,199,160 B1 | 3/2001 | Echensperger et al. |
| 6,208,954 B1 | 3/2001 | Houtchens |
| 6,231,812 B1 | 5/2001 | Rothberg et al. |
| 6,242,743 B1 | 6/2001 | DeVito et al. |
| 6,256,308 B1 | 7/2001 | Carlsson |
| 6,290,648 B1 | 9/2001 | Kamiyama |
| 6,301,495 B1 | 10/2001 | Gueziec et al. |
| 6,311,263 B1 | 10/2001 | Barlow et al. |
| 6,324,165 B1 | 11/2001 | Fan et al. |
| 6,331,116 B1 | 12/2001 | Kaufman et al. |
| 6,343,936 B1 | 2/2002 | Kaufman et al. |
| 6,369,209 B1 | 4/2002 | Manoharan et al. |
| 6,371,862 B1 | 4/2002 | Reda |
| 6,381,562 B2 | 4/2002 | Keane |
| 6,415,171 B1 | 7/2002 | Gueziec et al. |
| 6,421,612 B1 | 7/2002 | Agrafiotis et al. |
| 6,470,071 B1 | 10/2002 | Baertsch et al. |
| 6,477,370 B1 | 11/2002 | Sigler et al. |
| 6,490,476 B1 | 12/2002 | Townsend et al. |
| 6,504,895 B1 | 1/2003 | Dixon et al. |
| 6,510,541 B1 | 1/2003 | Fujiwara et al. |
| 6,523,079 B2 | 2/2003 | Kikinis et al. |
| 6,560,528 B1 | 5/2003 | Gitlin et al. |
| 6,567,690 B2 | 5/2003 | Giller et al. |
| 6,617,442 B1 | 9/2003 | Crooke et al. |
| 6,624,823 B2 | 9/2003 | Deering |
| 6,635,030 B1 | 10/2003 | Bae et al. |
| 6,636,721 B2 | 10/2003 | Threadgill et al. |
| 6,665,555 B2 | 12/2003 | Henderson et al. |
| 6,726,638 B2 | 4/2004 | Ombrellaro |
| 6,745,072 B1 | 6/2004 | Badura et al. |
| 6,745,160 B1 | 6/2004 | Ashar et al. |
| 6,753,873 B2 | 6/2004 | Dixon et al. |
| 6,772,026 B2 | 8/2004 | Bradbury et al. |
| 6,793,496 B2 | 9/2004 | Edic et al. |
| 6,794,879 B2 | 9/2004 | Lawson et al. |
| 6,845,489 B1 | 1/2005 | Mizuno et al. |
| 6,850,497 B1 | 2/2005 | Sigler et al. |
| 6,850,577 B2 | 2/2005 | Li |
| 6,868,092 B1 | 3/2005 | Bell et al. |
| 6,901,159 B2 | 5/2005 | Baertsch et al. |
| 6,904,124 B2 | 6/2005 | Staver et al. |
| 6,934,832 B1 | 8/2005 | Van Dyke et al. |
| 6,957,341 B2 | 10/2005 | Rice et al. |
| 6,958,627 B2 | 10/2005 | Singh et al. |
| 6,972,972 B2 | 12/2005 | Duncan et al. |
| 6,973,158 B2 | 12/2005 | Besson |
| 6,975,752 B2 | 12/2005 | Dixon et al. |
| 6,983,321 B2 | 1/2006 | Trinon et al. |
| 6,983,618 B2 | 1/2006 | Singh et al. |
| 6,987,831 B2 | 1/2006 | Ning |
| 7,002,910 B2 | 2/2006 | Garcia-Luna-Aceves et al. |
| 7,009,348 B2 | 3/2006 | Mogilner et al. |
| 7,013,257 B1 | 3/2006 | Nolan et al. |
| 7,023,979 B1 | 4/2006 | Wu et al. |
| 7,035,284 B2 | 4/2006 | Willenegger et al. |
| 7,046,618 B2 | 5/2006 | Santhoff et al. |
| 7,046,631 B1 | 5/2006 | Giroux et al. |
| 7,047,394 B1 | 5/2006 | Van Dyke et al. |
| 7,051,309 B1 | 5/2006 | Crosetto |
| 7,054,867 B2 | 5/2006 | Bosley et al. |
| 7,069,068 B1 | 6/2006 | Åstergaard |
| 7,077,967 B2 | 7/2006 | Perkins et al. |
| 7,087,008 B2 | 8/2006 | Fox et al. |
| 7,127,095 B2 | 10/2006 | El Fakhri et al. |
| 7,173,265 B2 | 2/2007 | Miller et al. |
| 7,194,117 B2 | 3/2007 | Kaufman et al. |
| 7,198,897 B2 | 4/2007 | Wangh et al. |
| 7,272,111 B2 | 9/2007 | Zukerman et al. |
| 7,272,766 B2 | 9/2007 | Sakezles |
| 7,289,599 B2 | 10/2007 | Seppi et al. |
| 7,292,552 B2 | 11/2007 | Willenegger et al. |
| 7,360,094 B2 | 4/2008 | Neff |
| 7,371,068 B2 | 5/2008 | Lloyd et al. |
| 7,371,538 B2 | 5/2008 | Simpson et al. |
| 7,406,065 B2 | 7/2008 | Willenegger et al. |
| 7,412,488 B2 | 8/2008 | Jha et al. |
| 7,420,931 B2 | 9/2008 | Nanda et al. |
| 7,438,685 B2 | 10/2008 | Burette et al. |
| 7,453,076 B2 | 11/2008 | Welch et al. |
| 7,480,362 B2 | 1/2009 | Carmi |
| 7,532,705 B2 | 5/2009 | Yin et al. |
| 7,570,656 B2 | 8/2009 | Raphaeli et al. |
| 7,594,889 B2 | 9/2009 | St Ores et al. |
| 7,603,182 B2 | 10/2009 | Sano et al. |
| 7,607,440 B2 | 10/2009 | Coste-Maniere et al. |
| 7,611,653 B1 | 11/2009 | Elsner et al. |
| 7,627,360 B2 | 12/2009 | Kimura |
| 7,676,034 B1 | 3/2010 | Wu et al. |
| 7,680,244 B2 | 3/2010 | Gertner et al. |
| 7,680,314 B2 | 3/2010 | Hong |
| 7,693,563 B2 | 4/2010 | Suresh et al. |
| 7,720,521 B2 | 5/2010 | Chang et al. |
| 7,731,499 B2 | 6/2010 | Sze et al. |
| 7,738,624 B2 | 6/2010 | Herold et al. |
| 7,744,913 B2 | 6/2010 | Noyes |
| 7,774,444 B1 | 8/2010 | George et al. |
| 7,792,249 B2 | 9/2010 | Gertner et al. |
| 7,801,271 B2 | 9/2010 | Gertner et al. |
| 7,805,518 B1 | 9/2010 | Kamvar et al. |
| 7,818,084 B2 | 10/2010 | Boyden et al. |
| 7,822,466 B2 | 10/2010 | Stoianovici et al. |
| 7,835,280 B2 | 11/2010 | Pang et al. |
| 7,841,986 B2 | 11/2010 | He et al. |
| 7,844,320 B2 | 11/2010 | Shahidi |
| 7,849,115 B2 | 12/2010 | Reiner |
| 7,941,236 B2 | 5/2011 | Spearman |
| 7,961,845 B2 | 6/2011 | Gertner et al. |
| 7,964,706 B2 | 6/2011 | Wu et al. |
| 8,002,465 B2 | 8/2011 | Ahn |
| 8,015,271 B2 | 9/2011 | McKeown et al. |
| 8,060,017 B2 | 11/2011 | Schlicht et al. |
| 8,060,340 B2 | 11/2011 | Gao et al. |
| 8,082,051 B2 | 12/2011 | Mihelich et al. |

(56) References Cited

U.S. PATENT DOCUMENTS

| | | |
|---|---|---|
| 8,095,382 B2 | 1/2012 | Boyden et al. |
| 8,109,865 B2 | 2/2012 | Jackson |
| 8,127,121 B2 | 2/2012 | Yates, Jr. et al. |
| 8,140,713 B2 | 3/2012 | Casper et al. |
| 8,147,537 B2 | 4/2012 | Boyden et al. |
| 8,163,003 B2 | 4/2012 | Boyden et al. |
| 8,170,855 B2 | 5/2012 | Jones et al. |
| 8,252,182 B1 | 8/2012 | Chang et al. |
| 8,311,791 B1 | 11/2012 | Avisar |
| 8,358,818 B2 | 1/2013 | Miga et al. |
| 8,457,930 B2 | 6/2013 | Schroeder |
| 8,476,013 B2 | 7/2013 | Ehrich et al. |
| 8,514,825 B1 | 8/2013 | Addepalli et al. |
| 8,515,058 B1 | 8/2013 | Gentry |
| 8,543,234 B2 | 9/2013 | Gao |
| 8,781,197 B2 | 7/2014 | Wang et al. |
| 8,792,965 B2 | 7/2014 | Ning et al. |
| 8,805,660 B2 | 8/2014 | Guyaguler et al. |
| 8,831,205 B1 | 9/2014 | Wu et al. |
| 8,849,633 B2 | 9/2014 | Core et al. |
| 8,891,849 B2 | 11/2014 | Rohler et al. |
| 8,892,198 B2 | 11/2014 | Bohorquez et al. |
| 9,113,808 B2 | 8/2015 | Bohorquez et al. |
| 9,323,896 B2 | 4/2016 | Falt et al. |
| 9,436,989 B2 | 9/2016 | Uber, III |
| 9,449,417 B1 | 9/2016 | Iben et al. |
| 9,744,195 B2 | 8/2017 | Xu |
| 9,788,905 B2 | 10/2017 | Avisar |
| 2002/0007294 A1 | 1/2002 | Bradbury et al. |
| 2002/0050979 A1 | 5/2002 | Oberoi et al. |
| 2002/0103622 A1 | 8/2002 | Burge |
| 2002/0172987 A1 | 11/2002 | Terstappen et al. |
| 2003/0045803 A1 | 3/2003 | Acharya |
| 2003/0073092 A1 | 4/2003 | Maranas et al. |
| 2003/0076331 A1 | 4/2003 | Deering |
| 2003/0083565 A1 | 5/2003 | Toth et al. |
| 2003/0099951 A1 | 5/2003 | Akeson et al. |
| 2003/0105799 A1 | 6/2003 | Khan et al. |
| 2003/0125924 A1 | 7/2003 | Lines et al. |
| 2003/0128801 A1 | 7/2003 | Eisenberg et al. |
| 2003/0163593 A1 | 8/2003 | Knightly |
| 2003/0220557 A1 | 11/2003 | Cleary et al. |
| 2004/0005089 A1 | 1/2004 | Robles et al. |
| 2004/0006274 A1 | 1/2004 | Giller et al. |
| 2004/0054505 A1 | 3/2004 | Lee |
| 2004/0064582 A1 | 4/2004 | Raghunath et al. |
| 2004/0082510 A1 | 4/2004 | Ullrich et al. |
| 2004/0106553 A1 | 6/2004 | Alekshun et al. |
| 2004/0107084 A1 | 6/2004 | Arakelyan et al. |
| 2004/0110110 A1 | 6/2004 | Chishti et al. |
| 2004/0131543 A1 | 7/2004 | Wong et al. |
| 2004/0131998 A1 | 7/2004 | Marom et al. |
| 2004/0136336 A1 | 7/2004 | Nakamura et al. |
| 2004/0152036 A1 | 8/2004 | Abolfathi et al. |
| 2004/0167731 A1 | 8/2004 | Wang et al. |
| 2004/0197728 A1 | 10/2004 | Abolfathi et al. |
| 2004/0209234 A1 | 10/2004 | Geiger |
| 2004/0234113 A1 | 11/2004 | Miga |
| 2004/0236216 A1 | 11/2004 | Manjeshwar et al. |
| 2004/0236550 A1 | 11/2004 | Edic et al. |
| 2004/0240604 A1 | 12/2004 | Wang et al. |
| 2005/0008628 A1 | 1/2005 | Feld et al. |
| 2005/0048456 A1 | 3/2005 | Chefd'hotel et al. |
| 2005/0053950 A1 | 3/2005 | Ubani et al. |
| 2005/0063575 A1 | 3/2005 | Ma et al. |
| 2005/0080332 A1 | 4/2005 | Shiu et al. |
| 2005/0100201 A1 | 5/2005 | Mayer et al. |
| 2005/0111621 A1 | 5/2005 | Riker et al. |
| 2005/0112590 A1 | 5/2005 | Boom et al. |
| 2005/0129170 A1 | 6/2005 | Watson et al. |
| 2005/0170323 A1 | 8/2005 | Jarrell et al. |
| 2005/0170528 A1 | 8/2005 | West et al. |
| 2005/0193048 A1 | 9/2005 | Vaudenay et al. |
| 2005/0203988 A1 | 9/2005 | Nollet et al. |
| 2005/0209888 A1 | 9/2005 | Oowaki et al. |
| 2005/0239182 A1 | 10/2005 | Berzin |
| 2005/0267348 A1 | 12/2005 | Wollenweber et al. |
| 2006/0025931 A1 | 2/2006 | Rosen et al. |
| 2006/0063141 A1 | 3/2006 | McGann et al. |
| 2006/0067461 A1 | 3/2006 | Yin et al. |
| 2006/0075211 A1 | 4/2006 | Vorbach |
| 2006/0090136 A1 | 4/2006 | Miller et al. |
| 2006/0104901 A1 | 5/2006 | Moodycliffe et al. |
| 2006/0115844 A1 | 6/2006 | Finkelstein et al. |
| 2006/0118465 A1 | 6/2006 | de Lasa |
| 2006/0122864 A1 | 6/2006 | Gottesman et al. |
| 2006/0161052 A1 | 7/2006 | Colombet et al. |
| 2006/0173268 A1 | 8/2006 | Mullick et al. |
| 2006/0224326 A1 | 10/2006 | St Ores et al. |
| 2006/0252061 A1 | 11/2006 | Zabeau et al. |
| 2006/0269049 A1 | 11/2006 | Yin et al. |
| 2007/0014452 A1 | 1/2007 | Suresh et al. |
| 2007/0015994 A1 | 1/2007 | Hong et al. |
| 2007/0016034 A1 | 1/2007 | Donaldson |
| 2007/0027667 A1 | 2/2007 | Osborn et al. |
| 2007/0041490 A1 | 2/2007 | Jha et al. |
| 2007/0043597 A1 | 2/2007 | Donaldson |
| 2007/0061016 A1 | 3/2007 | Kuo et al. |
| 2007/0076842 A1 | 4/2007 | Tkaczyk et al. |
| 2007/0076846 A1 | 4/2007 | Ruchala et al. |
| 2007/0092018 A1 | 4/2007 | Fonseka et al. |
| 2007/0106157 A1 | 5/2007 | Kaczkowski et al. |
| 2007/0115282 A1 | 5/2007 | Turner et al. |
| 2007/0115800 A1 | 5/2007 | Fonseka et al. |
| 2007/0118243 A1 | 5/2007 | Schroeder et al. |
| 2007/0133736 A1 | 6/2007 | Chen et al. |
| 2007/0147686 A1 | 6/2007 | Joshi |
| 2007/0156123 A1 | 7/2007 | Moll et al. |
| 2007/0159962 A1 | 7/2007 | Mathavu et al. |
| 2007/0164167 A1 | 7/2007 | Bachelder et al. |
| 2007/0168057 A1 | 7/2007 | Blevins et al. |
| 2007/0178429 A1 | 8/2007 | Bell |
| 2007/0184467 A1 | 8/2007 | Rabinowitz et al. |
| 2007/0196007 A1 | 8/2007 | Chen et al. |
| 2007/0201613 A1 | 8/2007 | Lu et al. |
| 2007/0208252 A1 | 9/2007 | Makower |
| 2007/0239150 A1 | 10/2007 | Zvuloni et al. |
| 2007/0239409 A1 | 10/2007 | Alan |
| 2007/0249967 A1 | 10/2007 | Buly et al. |
| 2007/0260138 A1 | 11/2007 | Feldman et al. |
| 2007/0276225 A1 | 11/2007 | Kaufman et al. |
| 2007/0282263 A1 | 12/2007 | Kalafut et al. |
| 2007/0287906 A1 | 12/2007 | Kadir et al. |
| 2007/0288208 A1 | 12/2007 | Grigsby et al. |
| 2008/0010417 A1 | 1/2008 | Zeffer et al. |
| 2008/0015418 A1 | 1/2008 | Jarrell et al. |
| 2008/0015664 A1 | 1/2008 | Podhajsky |
| 2008/0037435 A1 | 2/2008 | Sankala |
| 2008/0064028 A1 | 3/2008 | Hirao et al. |
| 2008/0067068 A1 | 3/2008 | Li |
| 2008/0081963 A1 | 4/2008 | Naghavi et al. |
| 2008/0097197 A1 | 4/2008 | Kalafut et al. |
| 2008/0103391 A1 | 5/2008 | Dos Santos Varela |
| 2008/0103547 A1 | 5/2008 | Okun et al. |
| 2008/0107641 A1 | 5/2008 | Kuebler |
| 2008/0123920 A1* | 5/2008 | Toth ............... A61B 6/032 382/131 |
| 2008/0126812 A1 | 5/2008 | Ahmed et al. |
| 2008/0141072 A1 | 6/2008 | Kalgren et al. |
| 2008/0147465 A1 | 6/2008 | Raines et al. |
| 2008/0181472 A1 | 7/2008 | Doi et al. |
| 2008/0182220 A1 | 7/2008 | Chishti et al. |
| 2008/0187895 A1 | 8/2008 | Sakezles |
| 2008/0201007 A1 | 8/2008 | Boyden et al. |
| 2008/0212740 A1 | 9/2008 | Sakaguchi et al. |
| 2008/0214933 A1 | 9/2008 | Von Busch et al. |
| 2008/0240336 A1 | 10/2008 | Miyazaki et al. |
| 2008/0248443 A1 | 10/2008 | Chishti et al. |
| 2008/0271866 A1 | 11/2008 | Hong et al. |
| 2008/0275327 A1 | 11/2008 | Faarbaek et al. |
| 2008/0310582 A1 | 12/2008 | Flohr et al. |
| 2008/0314807 A1 | 12/2008 | Junghanns et al. |
| 2009/0006061 A1 | 1/2009 | Thukral et al. |
| 2009/0006129 A1 | 1/2009 | Thukral et al. |

(56) References Cited

U.S. PATENT DOCUMENTS

| | | |
|---|---|---|
| 2009/0011492 A1 | 1/2009 | Berzin |
| 2009/0018882 A1 | 1/2009 | Burton et al. |
| 2009/0024181 A1 | 1/2009 | Raghavan et al. |
| 2009/0046775 A1 | 2/2009 | Thiagarajan et al. |
| 2009/0055141 A1 | 2/2009 | Moncorge et al. |
| 2009/0061854 A1 | 3/2009 | Gillot et al. |
| 2009/0087494 A1 | 4/2009 | Kompella et al. |
| 2009/0099862 A1 | 4/2009 | Fireman et al. |
| 2009/0110145 A1 | 4/2009 | Lu et al. |
| 2009/0116616 A1 | 5/2009 | Lu et al. |
| 2009/0128553 A1 | 5/2009 | Perry et al. |
| 2009/0171203 A1 | 7/2009 | Avital et al. |
| 2009/0175418 A1 | 7/2009 | Sakurai et al. |
| 2009/0204785 A1 | 8/2009 | Yates, Jr. et al. |
| 2009/0221999 A1 | 9/2009 | Shahidi |
| 2009/0226867 A1 | 9/2009 | Kalafut et al. |
| 2009/0252291 A1 | 10/2009 | Lu et al. |
| 2009/0259312 A1 | 10/2009 | Shterling et al. |
| 2009/0259314 A1 | 10/2009 | Linder-Ganz et al. |
| 2009/0279626 A1 | 11/2009 | Wang |
| 2009/0287271 A1 | 11/2009 | Blum et al. |
| 2009/0298103 A1 | 12/2009 | Mann et al. |
| 2009/0311190 A1 | 12/2009 | Gracias et al. |
| 2009/0326336 A1 | 12/2009 | Lemke et al. |
| 2010/0008467 A1 | 1/2010 | Dussault et al. |
| 2010/0030073 A1 | 2/2010 | Kalafut |
| 2010/0081971 A1 | 4/2010 | Allison |
| 2010/0105011 A1 | 4/2010 | Karkar et al. |
| 2010/0113887 A1 | 5/2010 | Kalafut et al. |
| 2010/0125735 A1 | 5/2010 | Zapata et al. |
| 2010/0130878 A1 | 5/2010 | Lasso et al. |
| 2010/0131283 A1 | 5/2010 | Linthicum et al. |
| 2010/0140483 A1 | 6/2010 | Rousso et al. |
| 2010/0161301 A1 | 6/2010 | Arakelyan et al. |
| 2010/0185419 A1 | 7/2010 | Singh et al. |
| 2010/0191071 A1 | 7/2010 | Anderson et al. |
| 2010/0191088 A1 | 7/2010 | Anderson et al. |
| 2010/0191100 A1 | 7/2010 | Anderson et al. |
| 2010/0217660 A1 | 8/2010 | Biswas |
| 2010/0220832 A1 | 9/2010 | Ning et al. |
| 2010/0236929 A1 | 9/2010 | Pollack et al. |
| 2010/0261994 A1 | 10/2010 | Davalos et al. |
| 2010/0268223 A1 | 10/2010 | Coe et al. |
| 2011/0004827 A1 | 1/2011 | Doerr et al. |
| 2011/0007361 A1 | 1/2011 | Takahashi et al. |
| 2011/0054486 A1 | 3/2011 | Linder-Ganz et al. |
| 2011/0090795 A1 | 4/2011 | Li et al. |
| 2011/0092762 A1 | 4/2011 | Wong et al. |
| 2011/0092763 A1 | 4/2011 | Rabinowitz et al. |
| 2011/0093036 A1 | 4/2011 | Mashiach |
| 2011/0106221 A1 | 5/2011 | Neal, II et al. |
| 2011/0125539 A1 | 5/2011 | Bollapragada et al. |
| 2011/0137156 A1 | 6/2011 | Razzaque et al. |
| 2011/0142316 A1 | 6/2011 | Wang et al. |
| 2011/0142936 A1 | 6/2011 | Campbell et al. |
| 2011/0144967 A1 | 6/2011 | Adirovich |
| 2011/0159100 A1 | 6/2011 | Andersen et al. |
| 2011/0161977 A1 | 6/2011 | Vorbach |
| 2011/0164562 A1 | 7/2011 | Qiu et al. |
| 2011/0212440 A1 | 9/2011 | Viovy et al. |
| 2011/0255761 A1 | 10/2011 | O'Dell et al. |
| 2011/0257653 A1 | 10/2011 | Hughes et al. |
| 2011/0270123 A1 | 11/2011 | Reiner |
| 2011/0282181 A1 | 11/2011 | Wang et al. |
| 2011/0288877 A1 | 11/2011 | Ofek et al. |
| 2011/0291807 A1 | 12/2011 | Law et al. |
| 2011/0293619 A1 | 12/2011 | Kuferr et al. |
| 2011/0301662 A1 | 12/2011 | Bar-Yoseph et al. |
| 2011/0319746 A1 | 12/2011 | Kochba et al. |
| 2011/0320056 A1 | 12/2011 | Brown et al. |
| 2012/0004725 A1 | 1/2012 | Shterling et al. |
| 2012/0022843 A1 | 1/2012 | Ionasec et al. |
| 2012/0035476 A1 | 2/2012 | Barthe et al. |
| 2012/0041279 A1 | 2/2012 | Freeman et al. |
| 2012/0041685 A1 | 2/2012 | Ding et al. |
| 2012/0089812 A1 | 4/2012 | Smith |
| 2012/0095322 A1 | 4/2012 | Tsekos et al. |
| 2012/0121151 A1 | 5/2012 | Bernhardt et al. |
| 2012/0136194 A1 | 5/2012 | Zhang et al. |
| 2012/0148131 A1 | 6/2012 | Couch et al. |
| 2012/0150506 A1 | 6/2012 | Han et al. |
| 2012/0165202 A1 | 6/2012 | Porreca et al. |
| 2012/0179436 A1 | 7/2012 | Fung |
| 2012/0185020 A1 | 7/2012 | Simon et al. |
| 2012/0197619 A1 | 8/2012 | Yelin et al. |
| 2012/0215510 A1 | 8/2012 | Metaxas |
| 2012/0215560 A1 | 8/2012 | Ofek et al. |
| 2012/0245481 A1 | 9/2012 | Blanco et al. |
| 2012/0265050 A1 | 10/2012 | Wang |
| 2012/0265324 A1 | 10/2012 | Colombo et al. |
| 2013/0018641 A1 | 1/2013 | de Prisco et al. |
| 2013/0044791 A1 | 2/2013 | Rimini et al. |
| 2013/0054202 A1 | 2/2013 | Carlsen et al. |
| 2013/0066750 A1 | 3/2013 | Siddique et al. |
| 2013/0093829 A1 | 4/2013 | Rosenblatt et al. |
| 2013/0099941 A1 | 4/2013 | Jana et al. |
| 2013/0113802 A1 | 5/2013 | Weersink et al. |
| 2013/0135312 A1 | 5/2013 | Yang et al. |
| 2013/0151265 A1 | 6/2013 | Kos et al. |
| 2013/0166271 A1 | 6/2013 | Danielsson et al. |
| 2013/0166767 A1 | 6/2013 | Olivier |
| 2013/0167250 A1 | 6/2013 | Balasubramanian |
| 2013/0179061 A1 | 7/2013 | Gadh et al. |
| 2013/0187930 A1 | 7/2013 | Millman |
| 2013/0202079 A1 | 8/2013 | Yu et al. |
| 2013/0211247 A1 | 8/2013 | Kalafut |
| 2013/0215116 A1 | 8/2013 | Siddique et al. |
| 2013/0238304 A1 | 9/2013 | Glinsky |
| 2013/0317511 A1 | 11/2013 | Bojarski et al. |
| 2013/0324845 A1 | 12/2013 | Korporaal |
| 2013/0326639 A1 | 12/2013 | Droste et al. |
| 2013/0332128 A1 | 12/2013 | Miles et al. |
| 2013/0339958 A1 | 12/2013 | Droste et al. |
| 2014/0022250 A1 | 1/2014 | Mansi et al. |
| 2014/0024916 A1 | 1/2014 | Hautvast |
| 2014/0081659 A1 | 3/2014 | Nawana et al. |
| 2014/0088943 A1 | 3/2014 | Trayanova et al. |
| 2014/0105355 A1 | 4/2014 | Toimela et al. |
| 2014/0107390 A1 | 4/2014 | Brown et al. |
| 2014/0143509 A1 | 5/2014 | Vorbach |
| 2014/0151035 A1 | 6/2014 | Cohen et al. |
| 2014/0226783 A1 | 8/2014 | Ning et al. |
| 2014/0257047 A1 | 9/2014 | Sillay et al. |
| 2014/0270053 A1* | 9/2014 | Larson .................. A61B 6/032 378/4 |
| 2014/0276055 A1 | 9/2014 | Barthe et al. |
| 2014/0292333 A1 | 10/2014 | Beck et al. |
| 2014/0294273 A1 | 10/2014 | Jaisson |
| 2014/0294743 A1 | 10/2014 | Richard et al. |
| 2015/0042646 A1 | 2/2015 | Comaniciu et al. |
| 2015/0056591 A1 | 2/2015 | Tepper et al. |
| 2015/0088224 A1 | 3/2015 | Goldwasser et al. |
| 2015/0106596 A1 | 4/2015 | Vorbach et al. |
| 2015/0164457 A1 | 6/2015 | Nett et al. |
| 2015/0193575 A1 | 7/2015 | Houghton et al. |
| 2015/0213206 A1 | 7/2015 | Amarasingham et al. |
| 2015/0230766 A1 | 8/2015 | Wang et al. |
| 2015/0242324 A1 | 8/2015 | Novakovic et al. |
| 2015/0253284 A1 | 9/2015 | Sudarsan et al. |
| 2015/0286759 A1 | 10/2015 | Rehtanz et al. |
| 2015/0337631 A1 | 11/2015 | Matringe et al. |
| 2015/0347682 A1 | 12/2015 | Chen et al. |
| 2016/0025894 A1 | 1/2016 | Abou-Sayed et al. |
| 2016/0027340 A1 | 1/2016 | Chiribiri et al. |
| 2016/0071048 A1 | 3/2016 | Gujar et al. |
| 2016/0191714 A1 | 6/2016 | Johan et al. |
| 2016/0209837 A1 | 7/2016 | Kim |
| 2016/0253443 A1* | 9/2016 | Li ............................ G06F 19/30 703/2 |
| 2016/0287906 A1 | 10/2016 | Nord et al. |
| 2017/0135659 A1 | 5/2017 | Wang et al. |
| 2017/0281278 A1 | 10/2017 | Higaki et al. |
| 2017/0331563 A1 | 11/2017 | Tyler et al. |

(56) References Cited

U.S. PATENT DOCUMENTS

FOREIGN PATENT DOCUMENTS

| | | |
|---|---|---|
| CN | 101718856 A | 6/2010 |
| CN | 101900777 A | 12/2010 |
| CN | 102036389 A | 4/2011 |
| CN | 102072996 A | 5/2011 |
| CN | 102118819 A | 7/2011 |
| CN | 102254476 A | 11/2011 |
| CN | 202178009 A | 3/2012 |
| CN | 102612077 A | 7/2012 |
| CN | 102737392 A | 10/2012 |
| CN | 202488214 A | 10/2012 |
| CN | 103346846 A | 10/2013 |
| CN | 103761623 A | 4/2014 |
| CN | 103761895 A | 4/2014 |
| CN | 103761913 A | 4/2014 |
| CN | 203554462 U | 4/2014 |
| CN | 103777164 A | 5/2014 |
| DE | 102006060957 A1 | 6/2008 |
| EP | 1365545 | 11/2003 |
| EP | 1562332 | 8/2005 |
| EP | 1901153 | 3/2008 |
| FR | 2839894 | 11/2003 |
| FR | 2957251 | 9/2011 |
| GB | 2502168 A | 11/2013 |
| JP | H0747079 | 2/1995 |
| JP | H07253963 | 10/1995 |
| JP | 2003518280 | 6/2003 |
| JP | 2003310592 | 11/2003 |
| JP | 2005058284 | 3/2005 |
| JP | 2006502818 | 1/2006 |
| JP | 2007275183 | 10/2007 |
| JP | 2008110200 | 5/2008 |
| JP | 2009003527 | 1/2009 |
| JP | 2009160307 | 7/2009 |
| JP | 2009160308 | 7/2009 |
| JP | 2009160309 | 7/2009 |
| JP | 2009261519 | 11/2009 |
| JP | 2010524435 A | 7/2010 |
| JP | 2011164957 | 8/2011 |
| KR | 20090119241 | 11/2009 |
| KR | 20090119522 | 11/2009 |
| KR | 20100119103 | 11/2010 |
| KR | 20100119109 | 11/2010 |
| KR | 101324704 | 11/2013 |
| KR | 101371651 | 3/2014 |
| KR | 101572414 | 11/2015 |
| WO | WO1996038930 | 12/1996 |
| WO | WO1996038967 | 12/1996 |
| WO | WO1997020362 | 6/1997 |
| WO | WO1997037041 | 10/1997 |
| WO | WO2000014668 | 3/2000 |
| WO | WO2000057777 | 10/2000 |
| WO | WO2000062674 | 10/2000 |
| WO | WO2003065042 | 8/2003 |
| WO | WO2003091839 | 11/2003 |
| WO | WO2006020177 | 2/2006 |
| WO | WO2007043786 | 4/2007 |
| WO | WO2007062164 | 5/2007 |
| WO | 2007062619 A1 | 6/2007 |
| WO | WO2007114470 | 11/2007 |
| WO | WO2007129310 | 11/2007 |
| WO | 2008119567 A1 | 10/2008 |
| WO | WO2008122056 | 10/2008 |
| WO | WO2008127428 | 10/2008 |
| WO | WO2010067360 | 6/2010 |
| WO | WO2010105993 | 9/2010 |
| WO | WO2016168328 | 10/2016 |

\* cited by examiner

SYSTEM AND METHOD FOR GENERATING AND PERFORMING IMAGING PROTOCOL SIMULATIONS

BACKGROUND

The subject matter disclosed herein relates to medical imaging and, in particular, to a system and method for generating and performing imaging protocol simulations.

Typically, in computed tomography (CT) imaging systems, an X-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the X-ray beam by the subject. Each detector element of the detector array produces a separate electrical signal indicative of the attenuated beam received by each detector element. The electrical signals are transmitted to a data processing system for analysis which ultimately produces an image.

Generally, the X-ray source and the detector array are rotated about the gantry within an imaging plane and around the subject. X-ray sources typically include X-ray tubes, which emit the X-ray beam at a focal point. X-ray detectors typically include a collimator for collimating X-ray beams received at the detector, a scintillator for converting X-rays to light energy adjacent the collimator, and photodiodes for receiving the light energy from the adjacent scintillator and producing electrical signals therefrom. Typically, each scintillator of a scintillator array converts X-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using X-rays that are generated at a single polychromatic energy. However, some systems may obtain multi-energy images that provide additional information for generating images.

During scanning to acquire projection data, it is generally desirable to reduce X-ray dose received by the subject and to improve image quality. However, to develop protocols to achieve these goals usually involves some experimentation with patients to acquire knowledge that can be used retrospectively. In addition, feedback from the scanner utilized to acquire the image data may not be sufficient or useful in developing the protocols. Further, current techniques for developing protocols are limited in capability and do not provide enough prospective feedback (e.g., visual or quantitative) on the protocol's effect on an individual patient and/or across a patient population.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a computer-implemented method for generating and simulating a computed tomography (CT) protocol is provided. The method includes receiving, via a graphical user interface, at a processor user input including patient population size settings and scan technique settings for modeling the effects of the scan technique settings across a patient population as a function of patient size. The method also includes generating, via the processor, a patient population profile based on at least the patient population size settings and the scan technique settings, wherein the patient population profile includes specific CT scan technique settings to be applied across different size ranges of the patient population as a function of patient size. The method further includes displaying, on the graphical user interface, one or more visualization elements illustrating the effect of these specific CT scan technique settings on specific imaging metrics across the patient population.

In accordance with a second embodiment, a non-transitory computer-readable medium is provided. The computer-readable medium including processor-executable code that when executed by a processor causes the processor to receive, via a graphical user interface, user input including patient population size settings and scan technique settings for modeling the effects of the scan technique settings across a patient population as a function of patient size. The code also causes the processor to generate a patient population profile based on at least the patient population size settings and the scan technique settings, wherein the patient population profile includes specific CT scan technique settings to be applied across different size ranges of the patient population as a function of patient size. The code further causes the processor to display, on the graphical user interface, one or more visualization elements illustrating the effect of these specific CT scan technique settings on specific imaging metrics across the patient population.

In accordance with a third embodiment, a system is provided. The system includes a display and a processor. The processor is configured to execute instructions to receive, via a graphical user interface, user input including patient population size settings and scan technique settings for modeling the effects of the scan technique settings across a patient population as a function of patient size. The processor is also configured to execute instructions to generate a patient population profile based on at least the patient population size settings and the scan technique settings, wherein the patient population profile includes specific CT scan technique settings to be applied across different size ranges of the patient population as a function of patient size. The processor is further configured to display, on the graphical user interface, one or more visualization elements illustrating the effect of these specific CT scan technique settings on specific imaging metrics across the patient population.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
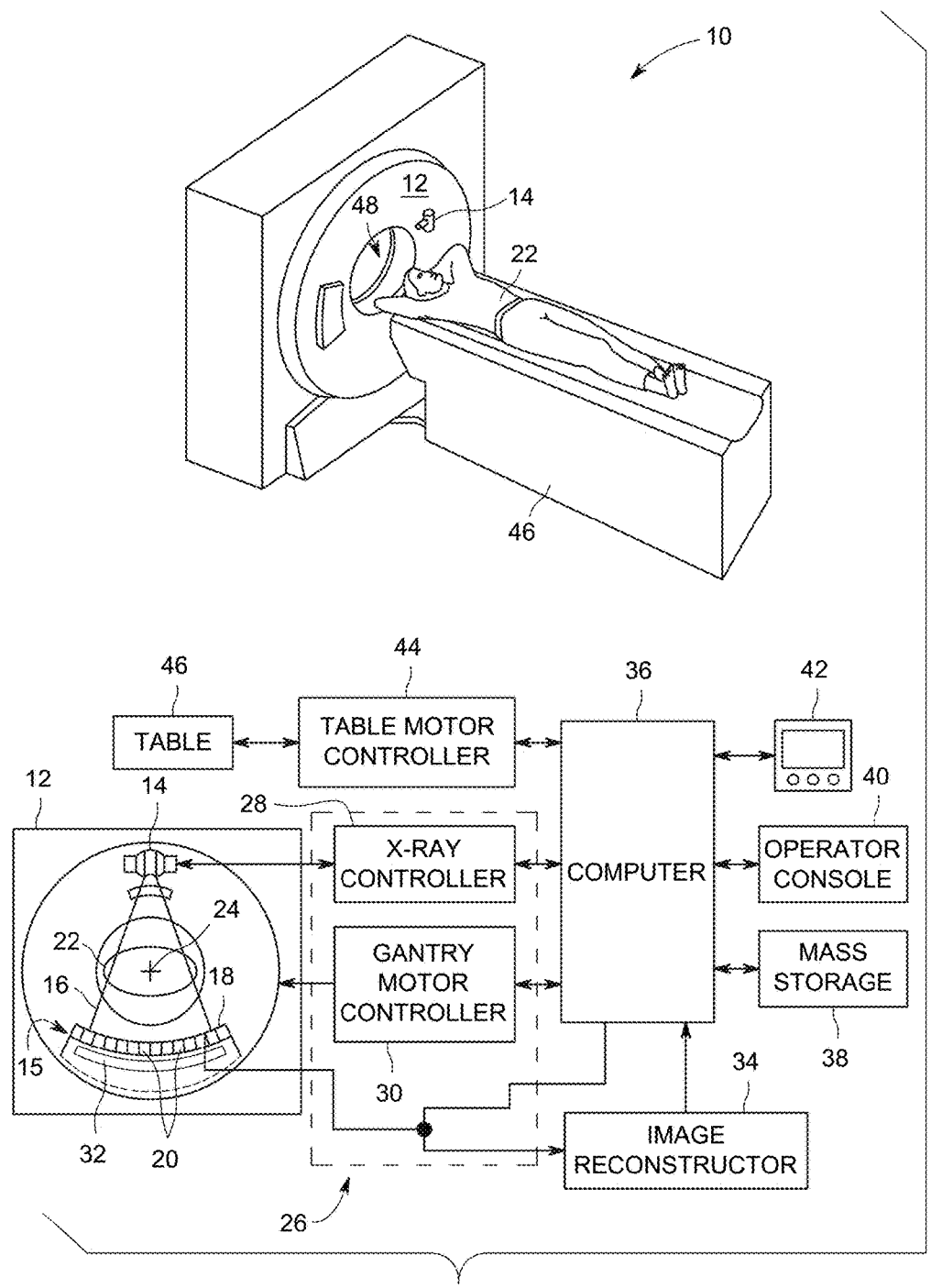
FIG. 1 is a combined pictorial view and block diagram of a computed tomography (CT) imaging system as discussed herein.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Disclosed herein are systems and methods for generating and performing imaging protocol simulations. In particular, a software-based tool is provided that enables a user to prescribe a scan technique profile (e.g., for a computed tomography (CT) system) as a function of patient size. A scan technique profile includes a plurality of scan technique settings or protocols for different size ranges over a patient population (e.g., a respective protocol (i.e., set of scan technique settings) for each respective size range of the patient population). The software-based tool also enables the user to receive immediate visual and quantitative dose and image quality feedback (e.g., via visualization elements such as graphs or tabular tables) on the effect of the profile across a patient population and/or an individual patient. Further, the effects of the profile on a patient population and/or an individual patient can be prospectively simulated. In certain embodiments, the software-based tool enables the user to model the effect of the profile between different states of the same system (e.g., same CT imaging system with different configurations in software and/or hardware) or between different CT systems. In certain embodiments, the patient population can be modeled with the software-based tool with an existing database of data or tailored to a specific patient population seen at the site where the CT scanner is employed to image the patient population. The software-based tool enables multiple functions on a single platform. The data utilized by the tool may be based on the patient population seen at the specific imaging site or imported from another site. In addition, the data utilized by the tool may be real clinical data or simulated clinical data of a single patient or across a patient demographic.

With the preceding in mind and referring to FIG. 1, a CT imaging system 10 is shown, by way of example. The CT imaging system includes a gantry 12. The gantry 12 has an X-ray source 14 that projects a beam of X-rays 16 toward a detector assembly 15 on the opposite side of the gantry 12. The detector assembly 15 includes a collimator assembly 18, a plurality of detector modules 20, and data acquisition systems (DAS) 32. The plurality of detector modules 20 detect the projected X-rays that pass through a patient 22, and DAS 32 converts the data to digital signals for subsequent processing. Each detector module 20 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position patient 22 and gantry 12. Particularly, table 46 moves portions of patient 22 through a gantry opening or bore 48.

As described in greater detail below, the computer 36 may include processing circuitry to execute instructions stored in a memory (e.g., on a non-transitory computer readable medium) of the computer or the mass storage device that enables a software-based tool to be utilized to generate and simulate CT scan protocols. In certain embodiments, the software-based tool may be utilized on a different computing device (e.g., another computer, tablet, or smartphone).

Figure 2:
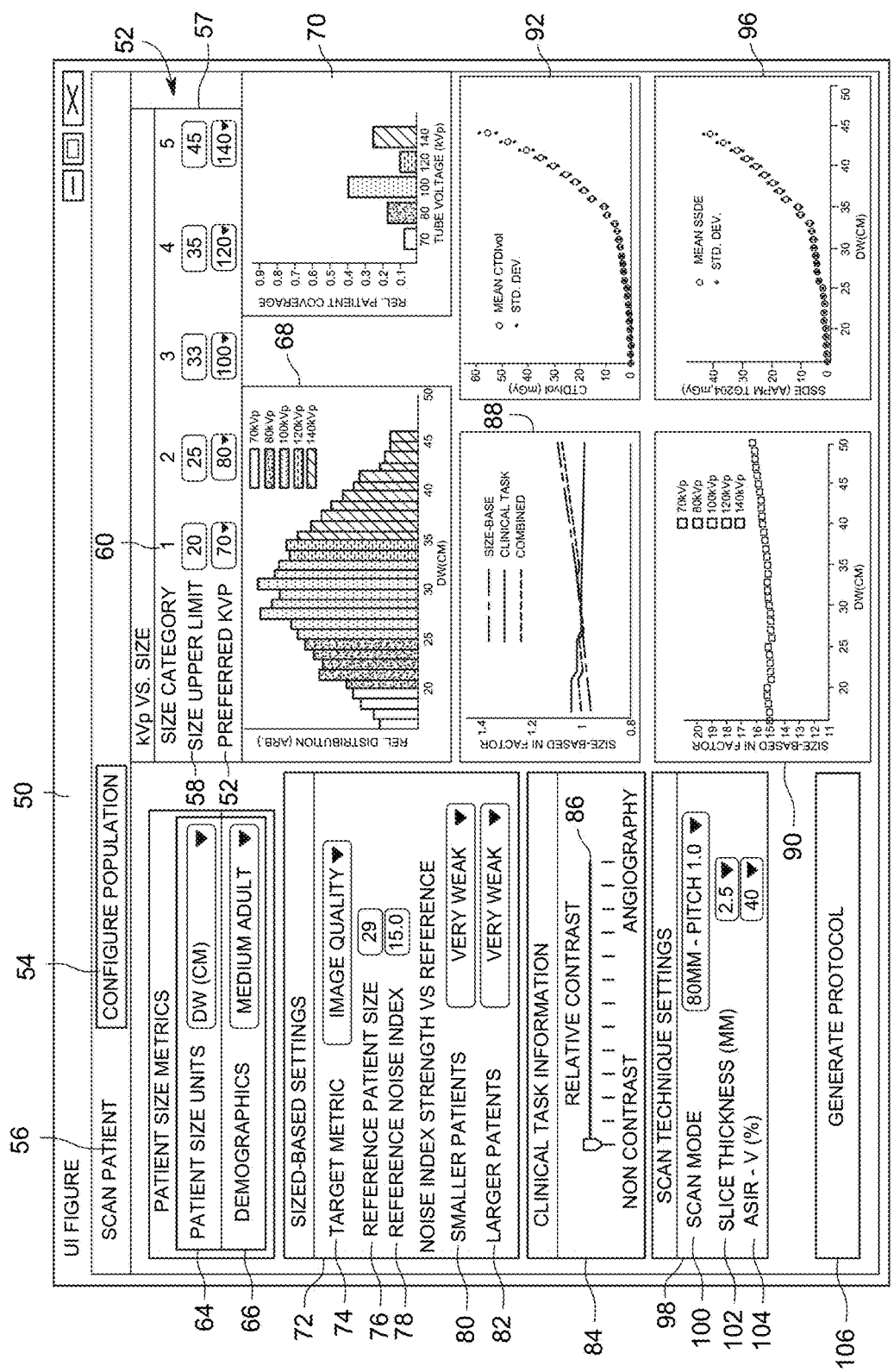
FIG. 2 is an embodiment of a display of a graphical user interface for configuring a patient population profile with a software-based tool.

FIG. 2 is an embodiment of a display 50 of a graphical user interface (GUI) 52 for configuring a patient population profile with a software-based tool. In other embodiments, certain aspects (e.g., settings, graphs, etc.) of the GUI may differ from the GUI 52 presented in FIG. 2. The GUI 52 enables the utilization of the software-based tool for generating and simulating CT protocols. As depicted, the GUI 52 includes tab 54 that enables utilization of the tool for modeling the effect of a chosen scan technique profile across a patient population (e.g., as a function of patient size). A scan technique profile includes a plurality scan technique settings or protocols for different size ranges over a patient population (e.g., a respective protocol (i.e., set of scan technique settings) for each respective size range of the patient population). As described in greater detail below (see FIG. 3), the GUI 52 also includes the tab 56 that enables utilization of the tool for prospectively simulating the effects of a scan protocol on an individual patient (e.g., utilizing the scan technique profile derived from the patient population).

As depicted in FIG. 2, tab 54 of the GUI 52 is selected. This enables the tool to be utilized to prescribe scan technique settings that vary with patient size. Besides scan technique settings, ancillary technique settings may also be prescribed (e.g., clinical task information such as the relative contrast in the scan). Further, under tab 54, the GUI 52 illustrates (e.g., via visualization elements such as graphs or tabular tables) visually and quantitatively the effect of the proscribed scan settings (and ancillary technique settings) on specific imaging metrics (e.g., dose specific metrics, image quality metrics, etc.). As mentioned, the tab 54 enables utilization of the tool for modeling the effect of a chosen scan technique profile across a patient population (e.g., as a function of patient size). Data for the patient population used in modeling the profile may be derived from an existing database of data or tailored for a patient population seen at a specific site. It should be noted a single patient represents a single operating point in the profile. In certain embodiments, the tool can be utilized to model the effect of the profile between different states of the same system (e.g., same CT imaging system with different configurations in software and/or hardware) or between different CT systems.

As depicted in FIG. 2, the GUI 52 includes an area 57 that enables the user to prospectively set size ranges per category bins where a chosen scan setting technique may be applied. For example, the upper limits 58 of different size ranges or bins 60 may be set. The number of bins 60 may vary. As depicted, 5 category bins are shown. A preferred peak kilovoltage (kVp) 62 is set for each respective bin 60 to set a specific kVp that a patient should be imaged at if the patient's anatomy size falls within the respective bin 60 or category. In certain embodiments, a scan technique (e.g., tube current or another scan technique) different from kVp may be specified (e.g., via drop down menu) for each bin 60 or category. The GUI 52 includes an area 64 for setting the patient size units for the size categories for modeling the patient size. The area 64 enables the selection of the patient size unit via a drop down menu. The patient size units may include standard weight metrics or non-standard weight metrics (e.g., used in medical imaging sites). Non-exhaustive examples of patient size units include weight (in pounds or kilograms), body mass index (e.g., in $kg/m^2$), water equivalent diameter (e.g., in cm), effective diameter, and various combinations of anatomical dimensions, such as the extent of anatomy in the Anterior-Posterior (AP) dimension or similar dimensions in the lateral (LAT) dimension (e.g., AP+LAT in cm). The GUI 52 also includes an area 66 for choosing the population size demographic information or model. For example, the area 66 may include a dropdown menu to select from among various size demographics such as large adult, medium adult, small adult, pediatric, etc. In certain embodiments, the demographic model may be derived from one of multiple existing models in existing databases of ergonomic dimensions. Alternatively, the demographic model can be specified by the user using a statistical model, imported from an alternate database, such as a cloud-based or online database of patient sizes. Also, the demographic model can be developed from sizing data from a radiology site, where the population is based on people seen at the site on a daily basis.

In certain embodiments, one or more visualization elements (e.g., graphs or plots) may be displayed on the GUI 52 breaking down patient demographic model relative to the chosen scan technique setting. For example, graph 68 illustrates each region of the patient demographic model chosen in area 66 that will be imaged using the kVp 62 for each bin or category 60. Specifically, graph 68 illustrates the respective proportions of the patient population (i.e., patient demographic model) to be imaged with each respective scan setting (i.e., kVp). The GUI 52 also includes an additional graph 70 that illustrates the same outcome in a different manner by illustrating a proportion of the patient population (i.e., patient demographic model) that will be imaged using each kVp setting. Any change in the technique settings of areas 57, 64, and 66 will be reflected in the graphs 68, 70.

The GUI 52 may include additional settings. For example, the GUI 52 includes area 72 for size-based techniques and target settings. Area 72 provides a field 74 (e.g., pull down menu) for a target metric (e.g., image quality, size based dose targets, or other technique settings.). As depicted, image quality is selected for field 74. In addition, area 72 includes a field 76 for inputting a reference patient size (utilizing the selected patient size units in area 64) and a field 78 for a reference noise index. The area 72 also includes fields 80, 82 (e.g., pull down menus) for defining how the prescribed target metric (in field 74) should vary as a function of patient size for smaller patients and larger patients, respectively, relative to the reference patient size. As depicted, the fields 80, 82 depict that the prescribed target metric (e.g., image quality) should vary very weakly if a patient is smaller than the reference patient size and if the patient is larger than the reference patient size. Alternatively, the variation can be chosen to be weak, strong, or very strong. In certain embodiments, other options for the user to select (e.g., via fields 80, 82) for determining how the target metric should vary in size may include a continuation variation per varying strengths, quantized per size category, constant without variation, a user-controlled custom variation, or any other possible variation profile.

The GUI 52 may also include an area 84 for providing clinical task information (e.g., via a slider 86) such as an indication of the expected relative contrast in the scans (e.g., due to a contrast injected into a patient habitus). The relative contrast may vary from a non-contrast scan to a maximum for certain types of scans (e.g., angiography).

The GUI 52 includes additional graphs simulating or modeling the effect of the chosen scan settings on specific imaging metrics across the patient population. Quantitative estimation may include (but is not limited to) radiation dose as measured by standard metrics such as CTDIvol or organ dose. Quantitative estimation for image quality effects may include (but is not limited to) estimated or projected pixel standard deviation within a defined region of the patient anatomy. Other changes in standard or non-standard image quality metrics may include noise, resolution, modulation transfer function, or object detectability. Visualization of feedback may be provided in graphical or tabular form of the profile technique settings as a function of patient size and the changes to the dose and/or image quality in response to changes in the profile. For example, graph 88 illustrates the prescribed relative variation in the target metric (e.g., size-based noise index factor) as a function of size. Graph 88 illustrates the relative variation in the noise metric between the size-based variation, the clinical task based variation, and a combined relative variation (i.e., final relative variation) of the size-based and clinical task based variation as a function of size. In the illustrated example, the relative reference target metric is equal to unity at the reference size.

Graph 90 illustrates the prescribed absolute variation in the target metric (e.g., noise index) as a function of patient size. As depicted in graph 90, the final absolute variation of the target metric as a function of size may be illustrated with color-coded variation with kVp. In the illustrated example, the absolute reference target metric is equal to the reference target metric at the reference size.

Graph 92 illustrates CTDIvol as a function of various metrics. CTDIvol is a single value provided to estimate the relative dose for an exam. Specifically, CTDIvol is a weighted average measurement (e.g., expressed in milliGrays) in a reference phantom. The graph 92 includes a field 94 (e.g., pull down menu) for the desired metric. As depicted, size is selected and the graph illustrates the CTDI-vol as a function patient size. Alternatively, kVp may be selected. In certain embodiments, a specific size category or kVp category may be selected with field 94. Graph 96 illustrates the CTDIvol weighted as a function of patient size to illustrate how the various profile technique settings affect the dose applied to the patient. As depicted, the mean size-specific dose estimate and associated standard deviation as a function of patient size.

The GUI 52 may also include an area 98 that enables the selection of scan technique settings that will affect the dose applied to a patient (e.g., as a function of patient size). As depicted, the area 98 includes a field 100 for scan mode, a field 102 for slice thickness, and a field 104 for reconstruction (e.g., adaptive iterative statistical reconstruction (ASiR-V)).

Besides the CT scan techniques above, the tool may utilize other settings. These settings may include tube current, scanned field of view (bowtie), scan rotation speed, helical pitch, level of iterative or other acquisition or reconstruction techniques. The settings utilized with the tool may be modified for primary and subsequent scan acquisitions or reconstructions. In addition, the tool may utilize ancillary CT scan techniques that may be profiled or modeled (besides level image contrast in area 84).

Upon configuring the population profile, the user may generate the profile or protocol by selecting button 106 on the GUI 52. The profile generated via the GUI 52 may govern the technique settings applied to a patient scan when the patient is in the CT scanner.

Figure 3:
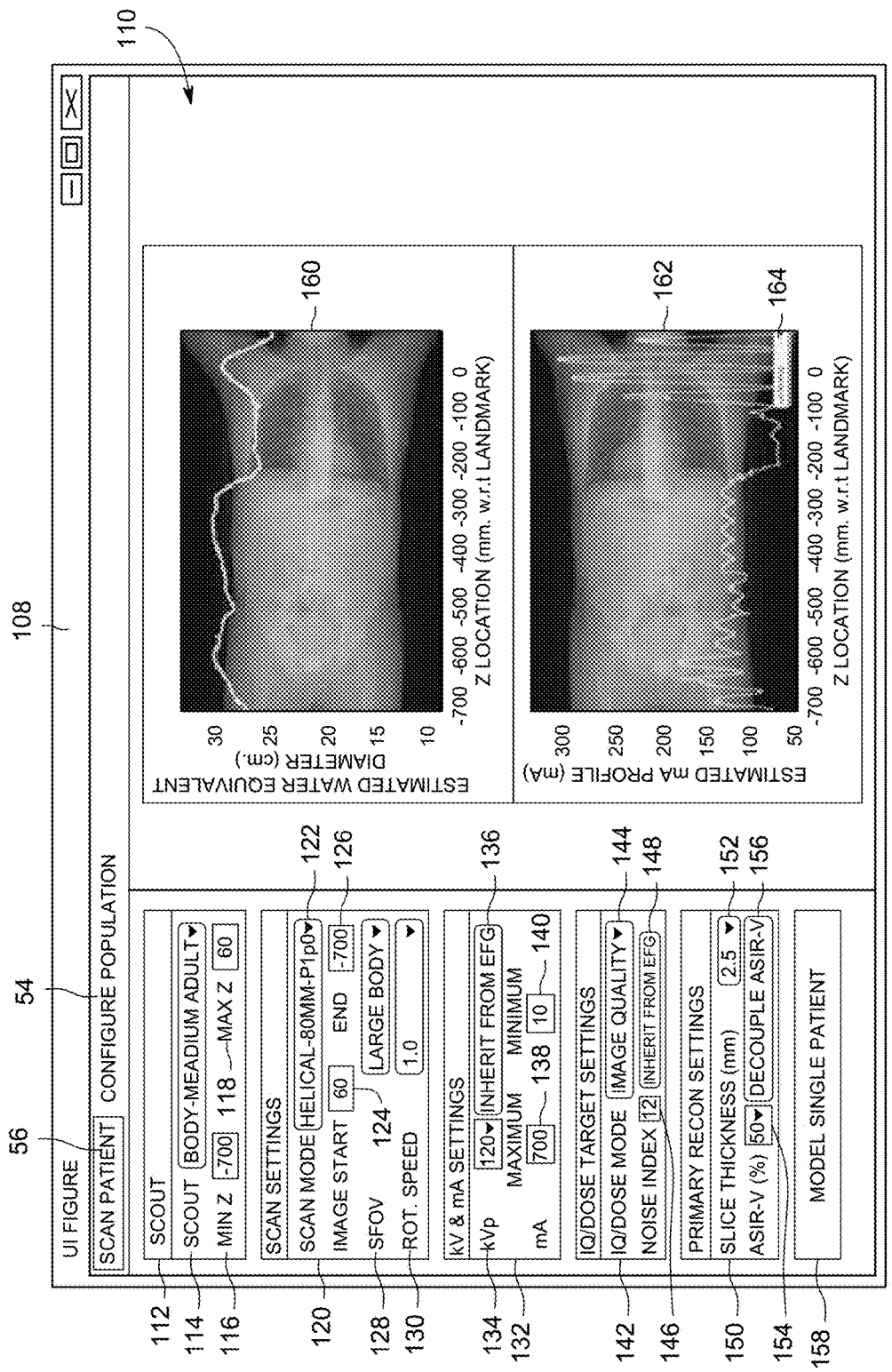
FIG. 3 is an embodiment of a display of a graphical user interface for simulating the effect of a patient population profile on an individual patient.

FIG. 3 is an embodiment of a display 108 of the GUI 110 for simulating the effect of a patient population profile on an individual patient. In other embodiments, certain aspects (e.g., settings, images, etc.) of the GUI may differ from the GUI 110 presented in FIG. 3. The GUI 110 also enables the utilization of the software-based tool for generating and simulating CT protocols. The GUI 110 is shown with selection of the tab 56 of the tool. The GUI 110 enables utilization of the tool for prospectively simulating the effects of a scan protocol on an individual patient (e.g., utilizing the scan technique profile derived from the patient population). The GUI 110 includes an area 112 that includes a field 114 (e.g., pull down menu) of a radiograph localizer (e.g., scout image such as a 2D X-ray) representative of an individual patient (large adult, medium adult, small adult, pediatric patient, etc.). The radiograph localizer may have been previously acquired and stored in a standard database of scout images or, alternatively, the radiograph localizer may have been imported directly from an actual patient at the imaging site. The area 112 also includes fields 116, 118 for adjusting parameters of the radiograph localizer (e.g., min Z, max Z, etc.). As an alternative to a radiograph localizer, a digital model may be utilized for the individual patient. The digital model may be derived from digital representations of patient anatomy based on solely software-based representations of generic patient populations. Alternatively, a digital representation made from digital reproductions of specific patients may be made from existing scouts.

The GUI 110 also includes an area 120 to adjust scan technique settings to be applied to the radiograph localizer. As depicted, the area 120 includes a field 122 (e.g., pull down menu) for scan mode, fields 124, 126 for inputting the start and end of the image, a field 128 (e.g., pull down menu) for scan field of view (SFOV) to determine how much of the patient anatomy is scanned, and a field 130 (e.g., pull down menu) for inputting the rotation speed for the gantry. The area 120 may include other scan technique settings.

The GUI 110 further includes an area 132 for setting the potential difference (kVp) across the X-ray tube and current (mA) of the X-ray tube. Specifically, the area 132 includes a field 134 (e.g., pull down menu) for selecting the kVp. In certain embodiments, the area 132 also includes a button 136 for importing the kVp from the scan profile previously defined for the patient population as described above. This enables the profile configured in tab 54 to be simulated on the radiograph localizer. The area 132 also includes fields 138, 140 for inputting the minimum and maximum mA, respectively, for the X-ray tube.

The GUI 110 still further includes an area 142 for setting specific image metrics (e.g., image quality and dose metrics). The area 142 includes a field 144 for selecting the desired image metric (e.g., image quality, dose, etc.). The area 142 also includes a field 146 for inputting a parameter or setting specific to the selected image metric. As depicted, the field 146 is for noise index. The parameter or setting for field 146 may be imported, via button 148, from the scan profile determined for the patient population as described above. This enables the profile configured in tab 54 to be simulated on the radiography localizer.

The GUI 110 even further includes an area 150 for primary reconstruction settings. For example, the area 150 may include a field 152 (e.g., pull down menu) for selecting the desired slice thickness. The area 150 also includes a field 154 (e.g., pull down menu) for ASiR-V and a button 156 for decoupling ASiR-V. The area 150 may include other primary reconstruction settings.

Upon inputting the various data and settings in areas 112, 120, 132, 142, and 150, the user may model or simulate these settings on the individual patient (i.e., the radiograph localizer) by selecting button 158 on the GUI 110. The GUI 110 may also display one or more images and visualization elements (e.g., associated graphs or plots) illustrating the effects of the selected data and settings on the individual patient (i.e., radio localizer) as well as simulates the effect of the patient population profile on the individual patient (when imported). For example, the GUI 110 provides an image 160 with associated plot providing feedback on the attenuation. For example, image 160 includes a plot for estimated water equivalent diameter within the selected scan range. The GUI 110 also provides an image 162 with associated plot for providing feedback on mA and image quality within the selected scan range. For example, image 162 includes a plot for estimated mA profile within the selected scan range. The image 162 may include a field 164 (e.g., pull down menu) for selecting between the desired parameter (e.g., mA profile, image quality parameter, etc.) to receive feedback for via the plot on the image 162.

The techniques above may also be utilized to compare the effects of technique settings between different CT systems or the same CT systems with different configurations (e.g., different software or hardware components). In certain embodiments, this may be achieved by matching image quality metrics and/or matching dose metrics. In other embodiments, this may be achieved by facilitating a voting-type system that enables the user to define a preferred perceived image quality based on selecting from reconstructed images presented to the user on the GUI for selection.

The techniques above may also be utilized to model the effect on image quality. In particular, the tool may enable modeling the effect on image quality of different technique settings on the image data sets utilizing modeled image data sets or actual acquired data sets of varying dose levels.

The techniques above may also be utilized to enable the user to indicate a preference for a specific type of reconstructed image for a single patient or across a patient population for a specific clinical imaging task. This may be achieved by the user using a single representative image or an amalgamation of chosen images (e.g., selected or voted on) across a database of representative images reconstructed under varying or different reconstruction techniques. The representative image or amalgamation can be interpreted via the tool to automatically translate the preferences into creating a profile of scan techniques that will result in output images that are largely representative of the desired image quality.

The software-based tool as illustrated in FIGS. 2 and 3 enables a user to prescribe a noise index across patient size within a single protocol. Equally, the tool enables the user to directly prescribe a patient exposure or patient 'dose' across patient size within a single protocol. Further, the tool enables the user to prescribe and model the effect of any technique setting on image quality and patient dose as a function of patient size. Even further, the tool enables within a single environment, the user to set specific scan techniques as a function of patient size. Yet further, the tool enables within a single environment, the user to model and visualize the effect of scan technique settings on patient exposure and modeled image quality. Still further, the tool enables within a single environment, the user to model the effect of scan technique settings on a patient population and on single individual patients. Further, the tool enables within a single environment, the user to model the effect of technique settings across patient populations across different CT systems or across different versions of the same CT system (e.g., different software or hardware components).

Figure 4:
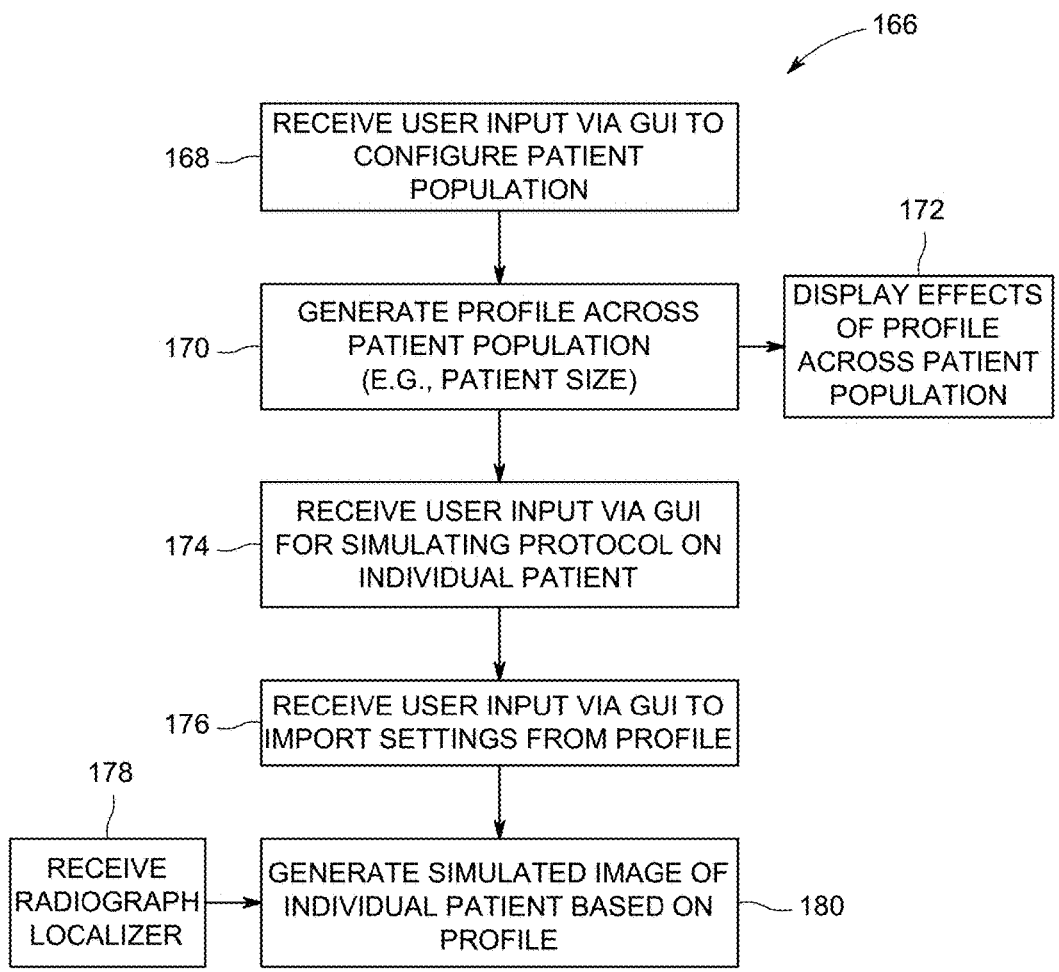
FIG. 4 is a flow chart an embodiment of a method for generating and simulating a computed tomography protocol.

FIG. 4 is a flow chart an embodiment of a method 166 for generating and simulating a computed tomography protocol (e.g., utilizing the software-based tool described above). One or more steps of the method 166 may be performed by the computer 36 (e.g., processing circuitry). One or more of the steps may be performed simultaneously or in a different order from that depicted in FIG. 4. The method 166 includes receiving a user input via a GUI to configure a patient population (block 168). For example, the GUI 52 shown in FIG. 2 or a variation of it may be utilized for providing inputs to the software-based tool. As described above, some of the inputs may include patient population size settings, scan technique settings, and other settings for modeling the effects of the scan technique settings across a patient population as a function of patient size. The method 166 also includes generating a profile across the patient population (e.g., as a function of patient size) (block 170). For example, the profile may be generated using the GUI 52 shown in FIG. 2 (or a variation thereof). The method 166 includes displaying (or modeling) the effects (e.g., visually and quantitatively) of the generated profile (e.g., as a function of size) on an imaging specific metric (e.g., image quality and/or dose) across the patient population (block 172). These may be presented via visualization elements including a combination of images, graphs, and tabular tables.

The method 166 also includes receiving a user input via a GUI for simulating the protocol on an individual patient (block 174). For example, the GUI 110 shown in FIG. 3 or a variation of it may be utilized for providing inputs to the software-based tool. As described above, some of the inputs may include scout settings, scan technique settings, image quality/dose settings, primary reconstruction settings, and other settings for modeling the effects of the profile on an individual patient. The method 166 further includes receiving a user input via a GUI for importing settings from the generated population profile (block 176). For example, as described above, GUI 110 in FIG. 3 may include buttons that associated with various settings (e.g. noise index, kVp, etc.) that enables the import of the profile to influence the scan technique settings applied to individual patient (and scout). The method 166 also includes receiving a radiograph localizer (e.g., scout) or digital representation or model of an individual patient (block 178). The method 166 further includes generating (and displaying) a simulated image of the individual patient based on the settings selected in GUI 110 along with any imported settings from the profile and the radiograph localizer (block 180). For example, as described above, the GUI 110 may provide one or more images and associated visualization elements (e.g., graphs or plots) illustrating the effects of the selected data and settings on the individual patient (i.e., radio localizer) as well as simulates the effect of the patient population profile on the individual patient (when imported). For example, as described above, the GUI 110 may provide an image with associated plot providing feedback on the attenuation or providing feedback on mA and image quality within the selected scan range.

Technical effects of the disclosed embodiments include providing a software-based tool is provided that enables a user to prescribe a scan technique profile (e.g., for a computed tomography (CT) system) as a function of patient size. The software-based tool also enables the user to receive immediate visual and quantitative dose and image quality feedback (e.g., via visualization elements such as graphs or tabular tables) on the effect of the profile across a patient population and/or an individual patient. Further, the effects of the profile on a patient population and/or an individual patient can be prospectively simulated. In certain embodiments, the software-based tool enables the user to model the effect of the profile between different states of the same system (e.g., same CT imaging system with different configurations in software and/or hardware) or between different CT systems. The software-based tool enables multiple functions on a single platform.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for generating and simulating a computed tomography (CT) protocol, comprising:

receiving, via a graphical user interface, at a processor user input comprising patient population size settings and scan technique settings for modeling the effects of the scan technique settings across a patient population as a function of patient size;

generating, via the processor, a patient population profile based on at least the patient population size settings and the scan technique settings, wherein the patient population profile comprises specific CT scan technique settings to be applied across different size ranges of the patient population as a function of patient size; and displaying, on the graphical user interface, one or more visualization elements illustrating the effect of these specific CT scan technique settings on specific imaging metrics across the patient population.

2. The computer-implemented method of claim 1, wherein the user input comprises clinical task information.

3. The computer-implemented method of claim 2, wherein the clinical task information comprises an expected relative level of contrast in a scan.

4. The computer-implemented method of claim 2, wherein the one or more visualization elements illustrate a variation in the specific imaging metrics across the patient population as a function of patient size, clinical task, and a combination of patient size and clinical task.

5. The computer-implemented method of claim 1, wherein the specific imaging metrics comprise dose specific metrics, image quality metrics, or both dose specific and image quality metrics.

6. The computer-implemented method of claim 1, wherein the patient population size settings comprise different size ranges and a preferred scan technique for each respective size range.

7. The computer-implemented method of claim 6, comprising displaying, on the graphical user interface, a graph representing respective proportions of the patient population to be imaged with a respective scan technique or a proportion of a respective size range to be imaged with the respective scan technique.

8. The computer-implemented method of claim 1, comprising:
receiving, at the processor, a radiograph localizer of an individual patient;
receiving, via the graphical user interface, at the processor additional scan technique settings, wherein some of the additional scan techniques are derived from the patient population profile; and
generating, via the processor, and displaying, via the graphical user interface, a simulated image of the individual patient based on the radiograph localizer and the additional scan technique settings.

9. The computer-implemented method of claim 8, wherein the additional scan technique settings comprise target image quality settings or target dose settings, primary image reconstruction settings, X-ray tube kilovoltage settings, X-ray tube current settings, scan specific settings, and/or scout specific settings.

10. A non-transitory computer-readable medium, the computer-readable medium comprising processor-executable code that when executed by a processor, causes the processor to:
receive, via a graphical user interface, user input comprising patient population size settings and scan technique settings for modeling the effects of the scan technique settings across a patient population as a function of patient size;
generate a patient population profile based on at least the patient population size settings and the scan technique settings, wherein the patient population profile comprises specific CT scan technique settings to be applied across different size ranges of the patient population as a function of patient size; and
display, on the graphical user interface, one or more visualization elements illustrating the effect of these specific CT scan technique settings on specific imaging metrics across the patient population.

11. The non-transitory computer readable storage medium of claim 10, wherein the user input comprises clinical task information.

12. The non-transitory computer readable storage medium of claim 11, wherein the clinical task information comprises an expected amount of contrast in a scan.

13. The non-transitory computer readable storage medium of claim 10, wherein the one or more visualization elements illustrate a variation in the specific imaging metrics across the patient population as a function of patient size, clinical task, and a combination of patient size and clinical task.

14. The non-transitory computer readable storage medium of claim 10, wherein the specific imaging metrics comprise dose specific metrics, image quality metrics, or both dose specific and image quality metrics.

15. The non-transitory computer readable storage medium of claim 10, wherein the patient population size settings comprise different size ranges and a preferred scan technique for each respective size range.

16. The non-transitory computer readable storage medium of claim 15, wherein the processor is further caused to display, on the graphical user interface, a graph representing respective proportions of the patient population to be imaged with a respective scan technique or a proportion of a respective size range to be imaged with the respective scan technique.

17. The non-transitory computer readable storage medium of claim 10, wherein the processor is further caused to:
receive a radiograph localizer of an individual patient;
receive, via the graphical user interface, additional scan technique settings, wherein some of the additional scan techniques are derived from the patient population profile; and
generate and display, via the graphical user interface, a simulated image of the individual patient based on the radiograph localizer and the additional scan technique settings.

18. The non-transitory computer readable storage medium of claim 10, wherein the additional scan technique settings comprise target image quality settings, target dose settings, primary image reconstruction settings, X-ray tube kilovoltage settings, X-ray tube current settings, scan specific settings, and/or scout specific settings.

19. A system, comprising:
a display; and
a processor configured to execute instructions to:
receive, via a graphical user interface, user input comprising patient population size settings and scan technique settings for modeling the effects of the scan technique settings across a patient population as a function of patient size;
generate a patient population profile based on at least the patient population size settings and the scan technique settings, wherein the patient population profile comprises specific CT scan technique settings to be applied across different size ranges of the patient population as a function of patient size; and
display, on the graphical user interface, one or more visualization elements illustrating the effect of these specific CT scan technique settings on specific imaging metrics across the patient population.

20. The system of claim 19, wherein the processor is further configured to:
receive a radiograph localizer of an individual patient;

receive, via the graphical user interface, additional scan technique settings, wherein some of the additional scan techniques are derived from the patient population profile; and generate and display, via the graphical user interface, a simulated image of the individual patient based on the radiograph localizer and the additional scan technique settings.

* * * * *